(12) United States Patent
Salmela et al.

(10) Patent No.: US 10,994,001 B2
(45) Date of Patent: May 4, 2021

(54) EDIBLE VACCINATION AGAINST MICROBIAL PATHOGENS

(71) Applicant: Dalan Animal Health Inc., Los Angeles, CA (US)

(72) Inventors: Heli Salmela, Helsinki (FI); Dalial Freitak, Helsinki (FI)

(73) Assignee: Dalan Animal Health Inc., Los Angeles, CA (US)

( * ) Notice: Subject to any disclaimer, the term of this patent is extended or adjusted under 35 U.S.C. 154(b) by 0 days.

(21) Appl. No.: 15/747,252

(22) PCT Filed: Jul. 22, 2016

(86) PCT No.: PCT/FI2016/050541
§ 371 (c)(1),
(2) Date: Jan. 24, 2018

(87) PCT Pub. No.: WO2017/017313
PCT Pub. Date: Feb. 2, 2017

(65) Prior Publication Data
US 2018/0214529 A1    Aug. 2, 2018

(30) Foreign Application Priority Data

Jul. 24, 2015 (FI) .................................... 20155564

(51) Int. Cl.
*A61K 39/02* (2006.01)
*A61K 39/09* (2006.01)
*A61K 39/00* (2006.01)

(52) U.S. Cl.
CPC .......... *A61K 39/0208* (2013.01); *A61K 39/02* (2013.01); *A61K 39/09* (2013.01); *A61K 2039/521* (2013.01); *A61K 2039/54* (2013.01); *A61K 2039/545* (2013.01); *A61K 2039/55* (2013.01); *A61K 2039/60* (2013.01)

(58) Field of Classification Search
CPC ................................................ A61K 39/0208
See application file for complete search history.

(56) References Cited

U.S. PATENT DOCUMENTS

| | | | | |
|---|---|---|---|---|
| 2015/0335689 | A1* | 11/2015 | Stamets | ............... A23K 20/163 424/195.15 |
| 2017/0035820 | A1* | 2/2017 | Stamets | ................. A61K 36/07 |

FOREIGN PATENT DOCUMENTS

| | | | |
|---|---|---|---|
| WO | WO 00/30435 | | 6/2000 |
| WO | WO 0030435 | * | 6/2000 |
| WO | WO 2010/128465 | | 11/2010 |
| WO | WO 2011/138310 | | 11/2011 |
| WO | WO 2011/138310 A2 | * | 11/2011 |
| WO | WO 2014/076261 | | 5/2014 |
| WO | WO 2015/077522 | | 11/2014 |

OTHER PUBLICATIONS

James et al., Insect Pathology, Chapter 12, 2012; 425-459 (Year: 2012).*
Chapter 8 Dead and Live attenuated vaccines http://apps.sanidadaninnal.info/cursos/innnnunology-old/octavo2.htm. , accessed Sep. 4, 2019 (Year: 2019).*
James et al., "From Silkworms to Bees: Diseases of Beneficial Insects" *Insect Pathology*, Chapter 12, Edited by Vega, F. and Kaya, H., pp. 425-459 (2012), ISBN: 978-0-12-384984-7.
Eggert et al., "Different effects of paternal trans-generational immune priming on survival and immunity in step and genetic offspring" *Proceedings of the Royal Society B*, vol. 281: 1-9 (2014), XP-002763117.
Finnish Office Action issued in Appln. No. 20155564 dated Mar. 3, 2016.
Freitak et al., "The maternal transfer of bacteria can mediate trans-generational immune priming in insects", *Virulence*, vol. 5, iss. 4: 547-554 (2014).
Havukainen et al., "Deconstructing honeybee vitellogenin: novel 40 kDa fragment assigned to its N terminus" *The Journal of Experimental Biology*, vol. 214: 582-592 (2011).
Havukainen et al., "Vitellogenin Recognizes Cell Damage through Membrane Binding and Shields Living Cells from Reactive Oxygen Species" *The Journal of Biological Chemistry*, vol. 288, No. 39: 28369-28381 (Sep. 27, 2013).
International Preliminary Report on Patentability issued in Appln. No. PCT/FI2016/050541 dated Nov. 2, 2017.
International Search Report issued in Appln. No. PCT/FI2016/050541 dated Nov. 11, 2016.
López et al., Trans-generational immune priming in honeybees *Proceedings of the Royal Society B*, vol. 281: 1-8 (2014).
Mikonranta et al., "Insect immunity: oral exposure to a bacterial pathogen elicits free radical response and protects from a recurring infection" *Frontiers in Zoology*, vol. 11, No. 23: 1-7 (2014).
Salmela et al., "Transfer of Immunity from Mother to Offspring Is Medicated via Egg-Yolk Protein Vitellogenin" *PLOS Pathogens*, vol. 11, No. 7: e1005015, 1-12 (2015), XP-062763118.
Seehuus al., "Immunogold localization of vitellogenin in the ovaries, hypopharyngeal glands and head fat bodies of honeybee workers, Apis mellifera" *Journal of Insect Science*, vol. 7, art. 52: 1-14 (2007).
Tong et al., "Vitellogenin is an acute phase protein with bacterial-binding and inhibiting activities" *Immunobiology*, Elsevier, vol. 215: 898-902 (2010).
Vallet-Gely et al., "Bacterial strategies to overcome insect defences" *Nature Reviews: Microbiology*, vol. 6: 302-313 (2008).

(Continued)

*Primary Examiner* — Gary B Nickol
*Assistant Examiner* — Lakia J Jackson-Tongue
(74) *Attorney, Agent, or Firm* — Foley & Lardner LLP

(57) ABSTRACT

The present invention relates to animals and more specifically to insects. In more details the invention relates to an edible composition or insect artificial diet comprising bacteria, fungi or any fragment or spore thereof for use as a vaccine in preventing a microbial disease or infection in an insect. Still, the present invention relates to preventive methods and different uses relating to said compositions or bacteria, fungi or fragments or spores thereof.

10 Claims, 10 Drawing Sheets

(56) References Cited

OTHER PUBLICATIONS

Figure 1:
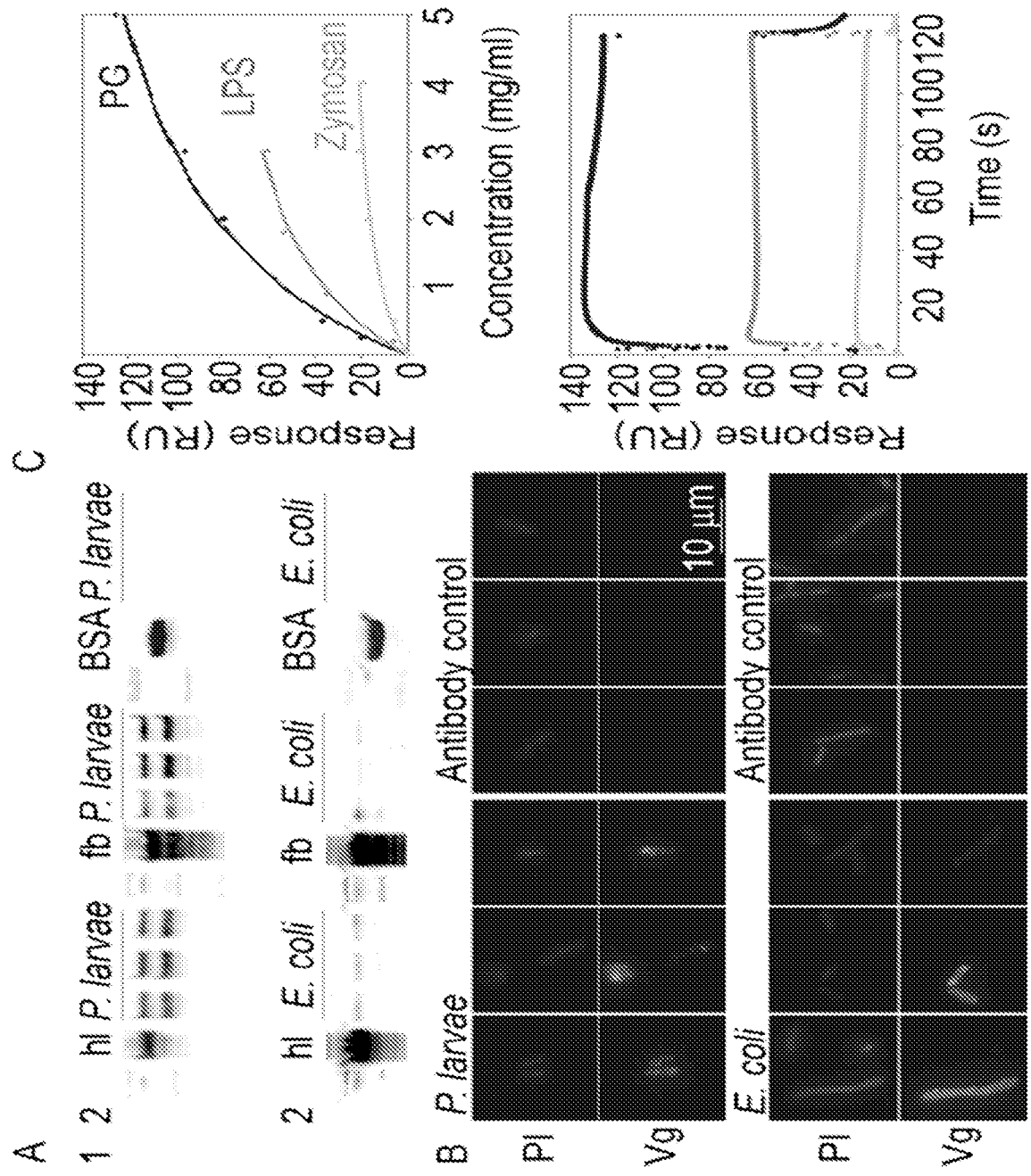

Wang et al., "Pathogen Entrapment by Transglutaminase—A Conserved Early Innate Immune Mechanism" *PLoS Pathogens,* vol. 6: iss. 2: e1000763, 1-9 2010.
Genersh, American Foulbrood in honeybees and its causative agent, *Paenibacillus larvae,* Journal of Invertebrate Pathology, vol. 103, pp. S10-S19 2010.

* cited by examiner

| Bacteria | Type of interaction | Host (mode of interaction) |
|---|---|---|
| *Erwinia aphidicola* | Pathogen | Pea aphid (ingestion) |
| *Dickeya dadantii* | Pathogen | Pea aphid (ingestion) |
| *Pseudomonas entomophila* | Pathogen | Drosophila, Bombyx, Galleria (ingestion) |
| *Yersinia pestis* | Pathogen | Rat flea (ingestion) |
| *Serratia entomophila* | Pathogen | Grass grub (ingestion) |
| *Serratia marcescens* | Pathogen | Drosophila (ingestion) |
| *Photorhabdus sp.* | Pathogen | Lepidopteran (assisted entry) |
| *Xenorhabdus sp.* | Pathogen | Lepidopteran (assisted entry) |
| *Vibrio cholerae* | Pathogen | Drosophila (ingestion) |
| *Melissococcus pluton* | Pathogen | Honey bee (ingestion) |
| *Bacillus thuringiensis* | Pathogen | Different orders (ingestion) |
| *Bacillus papillae* | Pathogen | Scarab larvae (ingestion) |
| *Paenibacillus lentimorbus* | Pathogen | Scarab larvae (ingestion) |
| *Paenibacillus larvae* | Pathogen | Honey bee larvae (ingestion) |
| *Bacillus sphaericus* | Pathogen | Mosquito (ingestion) |
| *Bacillus laterosporus* | Pathogen | Bee larvae, dipteran (ingestion) |
| *Pseudomonas aeruginosa* | Opportunistic | Caterpillar (ingestion) |
| *Pseudomonas aeruginosa* | Opportunistic | Drosophila (direct injection) |
| *Bacillus cereus* | Opportunistic | Galleria mellonella (ingestion) |
| *Erwinia carotovora* | Infectious | Drosophila larvae (ingestion) |
| *Shigella spp.* | Passive vector | House fly (ingestion) |
| *Rickettsia spp.* | Vector | Cat flea (ingestion) |
| *Bartonella spp.* | Vector | Cat flea (ingestion) |

Figure 5.

| Pathogen | Disease | General Signs and Symptoms | Some Distinct Characteristics | | |
|---|---|---|---|---|---|
| | | | Hemolymph | Midgut | Integument |
| Bacteria | | | | | |
| *Bacillus spp.* | Fuliginosa septicemia | Large thorax and small abdomen; anterior segments of abdomen with greenish black spots; vomiting and diarrhea; cadavers turn black, decayed and fetid | Brownish black. Bacteria abundant, large baciliform rods | Not distinct | Not distinct |
| *Serratia marcescens* | *Serratia*-type septicemia | Larvae with light specks; cadavers appear shortened, become flaccid, and turn pink or dark pink | Reddish brown. Bacteria abundant, short baciliform rods | Not distinct | Not distinct |
| *Aeromonas sp.* | Green thorax septicemia | Head and thorax of cadavers translucent green, and turned down ventrally; cadavers are flaccid and become putrid | Turbid. Bacteria present, small baciliform rods | Not distinct | Not distinct |
| *Bacillus thuringiensis* subsp. sotto (Bt sotto) | Sotto disease or bacillary paralysis | Larvae stop feeding, turn dark with internal nodules; posterior is translucent; cadavers turn flaccid | Not distinct | Midgut cells disassociating. Bacteria present, long baciliform rods. | Not distinct |
| *Enterococcus spp.* and other intestinal bacterial species | Bacterial flacherie; thoracic or wrinkling disease | Larvae not uniform in development, become thin and small. Diarrhea | Not distinct | Empty except for yellow-green mucus. Bacteria present, large, baciliform rods | Translucent on the head and thorax. |

FIG. 6

| Pathogen/mite | Disease | Known Hosts | Affected Host Stages | Signs and Symptoms |
|---|---|---|---|---|
| Bacteria | | | | |
| Melissococcus pluton | Foulbrood, European | Apis mellifera, Apis cerana | Larvae | Larvae typically die when 4-5 days old, and outbreaks usually occur in early summer. Dead larvae turn brown and flaccid. Midguts filled with bacteria in opaque white clumps. Dead larvae may dry to a scale that is rubbery and does not stick to the wax. Colonies typically recover. Melissococcus pluton cells ovoid to lanceolate (0.8 μm wide x 1.0 μm long), forms chains. Facultative anaerobe requires $CO_2$ |
| Paenibacillus larvae | Foulbrood, American | Apis mellifera, Apis cerana | Prepupae, pupae | Larvae die after spinning the cocoon, then turn putrid and dark brown, with a distinct fishy odor. If a toothpick is stuck into the larva and pulled out slowly, the remains draw out as brown, ropy thread. Discoloration is first seen when larvae reach 10-15 days old. Cell cappings sink in slightly, often with small hole in the center. After one month, the dead larvae dry to a small, flat scale that sticks to the wax. The bacterium is a Gram-positive bacillus, motile, with oval endospores (~2.5 x 0.5 μm, but highly variable in size) |
| Spiroplasma apis | May disease | Apis mellifera | Adults | Large numbers of adults found quivering and unable to fly, moribund or dead. Abdomens swollen and hard. Midgut full of undigested pollen. Other adults from the colony cluster in small groups away from the hive. Bees not dark and shiny, no obvious hair loss. Large numbers of adults may die in 4-5 weeks, but colonies usually recover. Wall-less, helical bacteria found in hemolymph and digestive tract |

FIG. 7

| Pathogen | Disease | General Signs and Symptoms | Some Distinct Characteristics | | |
|---|---|---|---|---|---|
| | | | Hemolymph | Midgut | Integument |
| Fungi: Filamentous | | | | | |
| Beauveria bassiana | White muscardine | Larvae sluggish, with oil-colored specks; cadavers soft at first and then stiffen, and finally covered with white conidia | Turbid. Becomes full of cylindrical hyphal bodies or hyphae | Not distinct | Larvae with powdery white appearance due to presence of large masses of globose conidia |
| Nomuraea rileyi | Green muscardine | Larvae sluggish, with oil-colored specks; cadavers soft at first and then stiffen, and finally covered with bright green conidia | Turbid. Gradually full of beaded hyphal bodies or hyphae | Not distinct | Presence of large masses of ovoid conidia results in bright green appearance |
| Aspergillus spp., e.g., A. flavus, A. ochraceus, A. oryzae, A. parasiticus, A. tamarii | Aspergillosis | Newly hatched larvae stop feeding, stop moving, frequent vomiting, and die in 2-3 days; late instars develop a lesion, thorax protrudes, frequent vomiting, die in 4-5 days; cadavers stiff with hyphae penetrating | Turbid. Hyphal bodies not present | Not distinct | Sporulation occurs in localized spots, color varies, often brown, usually dark. Hyphae visible around spots |
| Fungi: Microsporidia | | | | | |
| Nosema bombycis | Pébrine | Growth slow and typically asynchronous, molting may be incomplete; no cocoon formation; spores present in the hemolymph, midgut, silk gland, feces and eggs; ovoid 2.9-4.1 x 1.5-2.1 μm | Turbid, spores present | Swollen in appearance, ivory color with black specks | Sometimes peppered with black specks and thin, irregular setae |

FIG. 8

| Pathogen/mite | Disease | Known Hosts | Affected Host Stages | Signs and Symptoms |
|---|---|---|---|---|
| Fungi: filamentous | | | | |
| Ascosphaera apis | Chalkbrood | Apis mellifera | Larvae | Infected larvae die at a late stage, sometimes after the cell is capped. The dead larvae are hard, chalk-white, but often mottled with black spots (the fungal spores). Typically, adult bees remove infected larvae from the hive, and these dead larvae can be seen in large numbers near the hive entrance. Microscopic examination will reveal spores formed in sacs called ascomata, and within the ascomata are spore balls (ascospores). The ascospores are ovoid, but only slightly so, nearly spherical |
| Ascosphaera aggregata | Chalkbrood | Megachile rotundata | Larvae | Infected larvae most often die during the last instar, after they have consumed their entire pollen provision and reached full size, but before cocooning. Dead larvae are hard and black. The surface may easily disintegrate to a black powder (the fungal spores). Larvae may be mottled black and white, or be mostly white, but less commonly so than with chalkbrood in honey bee larvae. Ascospores are long ovoid, typically 2 μm wide and 4- 5 μm long |
| Ascosphaera torchoi | Chalkbrood | Osmia lignaria | Larvae | Similar to A. aggregata above. The ascospores are typically 2 μm wide and 4- 5 μm long |
| Aspergillus flavus and Aspergillus fumigatus | Stone brood | Apis mellifera | Larvae | Infected larvae die soon after cells are capped, before pupation, then turn very hard and pale brownish, gray, or yellow- green. The color comes from the spores. Spores are spherical and highly sculptured |
| Fungi: Microsporidia | | | | |
| Nosema apis | Dysentery | Apis mellifera | Adults | Disease characterized by the presence of spores in the midgut epithelium (~ 6 x 3 μm), and milky white appearance of the ventriculus. Usually < 30 coils to the polar filaments in the spores. No outward signs of infection, infected adults live about half as long as uninfected bees. Associated with dysentery in winter and early spring, but probably not the cause. Spread via fecal contamination |
| Nosema ceranae | Dysentery | Apis mellifera, Apis cerana | Adults | Disease characterized by the presence of spores in the midgut epithelium (~ 5 x 2 μm), with few distinct marks. Approx. 20 coils to the polar filaments in the spores. No outward signs of infection, infected adults live about half as long as uninfected bees. Associated with dysentery in winter and early spring, but probably not the cause. Spread via fecal contamination |
| Nosema bombi | Nosema disease | Bombus terrestris, Bombus occidentalis, Bombus impatiens | Adults | Disease characterized by the presence of spores throughout the body cavity (~4.2- 5.4 x 2.7- 3.5 μm), with few distinct marks. In B. terrestris and B. impatiens, colony growth and the production of reproductives are greatly reduced, but not with B. occidentalis. Transmission is transovarial and oral |

FIG. 9

EDIBLE VACCINATION AGAINST MICROBIAL PATHOGENS

This application is the U.S. national phase of International Application No. PCT/FI2016/050541 filed Jul. 22, 2016, which designated the U.S. and claims priority to FI Patent Application No. 20155564 filed Jul. 24, 2015, the entire contents of each of which are hereby incorporated by reference.

FIELD OF THE INVENTION

The present invention relates to animals and more specifically to insects. In more details the invention relates to an edible composition or insect artificial diet comprising bacteria, fungi or any fragment or spore thereof for use as a vaccine in preventing a microbial disease or infection in an insect. Still, the present invention relates to preventive methods and different uses relating to said compositions or bacteria, bacterial spores or fragments thereof. The present invention further relates to preventive methods and different uses relating to said compositions or fungi, fungal spores or fragments thereof.

BACKGROUND OF THE INVENTION

Insects have many important roles in the environment. For example insects may be used as food for people and animals, insects help in maintaining plant and animal diversity and also have enormous effect on the crop production. Insects ultimately affect humans since ensuring healthy crops is critical for agriculture. Insects also produce useful substances such as honey, wax, lacquer and silk. Therefore, the amount and health of insects are important ecological and economical issues. A serious environmental problem is the decline of populations of pollinator insects, and a number of species of insects are now cultured primarily for pollination management in order to have sufficient pollinators in the field, orchard or greenhouse at bloom time.

Insects are needed for pollination during the bloom period of the plants. Examples of well recognized pollinators are honey bees and the various species of bees but also many other kinds of pollinators are cultured and sold for managed pollination. Honey bees and other pollinators travel from flower to flower, collecting nectar, which is later converted to honey, and pollen grains. Pollinators transfer pollen among the flowers as they are working. Nectar provides the energy for bee nutrition and pollen provides the protein. When bees are rearing large quantities of brood, they gather pollen to meet the nutritional needs of the brood.

The Food and Agriculture Organisation of the United Nations (FAO) estimates that out of some 100 crop species which provide 90% of food worldwide, 71 are bee-pollinated. Honey bees are by far the most important commercial pollinators. However, at the same time, they are susceptible to many diseases, and thus like many other important pollinators, are in global population decline. In special focus in apiculture is the bacterial disease foulbrood that kills honey bee larvae. Foulbrood is common in most parts of the world, including Finland, and causes marked losses in corps worldwide. Currently foulbrood can be treated e.g. by burning up the whole hive. Also, the chemical oxytetracycline hydrochloride (antibiotic Terramycin) is used for prevention of foulbrood and tylosin (antibiotic Tylan) has been registered for therapeutic treatments of American foulbrood.

In addition to honey bees another example of an economically important insect is a primary producer of silk. Domestic silk moths are closely dependent on humans for reproduction, as a result of selective breeding. The silkworm is the larva or caterpillar of the domesticated silk moth (*Bombyx mori*). Thermal therapies have been developed for silk moth larva to control the flacherie virus disease. Also, e.g. disinfection and antibiotics are used against bacterial diseases. As an example, septicemias are common bacterial diseases in silkworms. *Serratia marcescens* is causing *Serratia*-type septicemia, *Bacillus* spp. is causing fuliginosa septicemia and *Aeromonas* bacteria is causing green thorax septicemia. The common symptoms of septicemia include that larvae become dull and motionless with reduced feeding rates, even resulting in mortality in late instar larvae.

Problems of the known treatment methods of insects having microbial diseases or infections include e.g. that the hives with infected honey bees must be totally destroyed and at the same time thermal methods are unreliable and may require moving of the hives. Furthermore, use of antibiotics lead to antibiotic resistance and antibiotics also stay in the environment e.g. the honey produced by honey bees contains the antibiotic. Actually, there is a lack of effective non-antibiotic methods for preventing microbial diseases of insects.

Recently, Lopez et al. (2014) have utilized trans-generational immune priming (TGIP) for priming the offspring of honey bees against infections. Indeed, Lopez et al. have shown that honey bee (*Apis mellifera*) queens injected with dead *Paenibacillus larvae* (bacterium responsible for the American foulbrood disease) produce significantly more foulbrood resistant larvae than non-injected queens. However, injecting insects at a large scale is not feasible, and the injecting techniques are not within reach of the insect farmers. Furthermore, very suitable and effective compositions are needed for continuous use.

In summary, there is a need of suitable and simple tools for preventing diseases and infections caused by microbial pathogens in insects.

BRIEF DESCRIPTION OF THE INVENTION

An object of the present invention is to provide a method and composition for implementing the method so as to solve the above mentioned problems. The present invention provides an edible pharmaceutical composition suitable for insects and preventing microbial diseases or infections.

The invention is based on the realization that immunization of insects can be utilized in preventing insect microbial diseases such as bacterial and fungal diseases by feeding the insects (e.g. larvae or adults) with said bacteria, fungi or any fragments or spores thereof. The preventive effect of the vaccine can be found in the insects fed with the vaccine composition, in the next generation or in both.

An advantage of the method and arrangement of the invention is that now there is available a non-antibiotic vaccination which is effective and can be easily used. By utilizing the present invention it is easy for anyone e.g. to mix the vaccine composition into normal insect artificial diet such as food for insects (e.g. honey bees, silk moth).

Furthermore, the present invention is able to reveal the detailed mechanism of how bacteria used for preventive therapeutic method are transported to insect eggs by a common insect lipoprotein vitellogenin (Vg).

The objects of the invention are achieved by a method and an arrangement, which are characterized by what is stated in the independent claims. The preferred embodiments of the invention are disclosed in the dependent claims.

The present invention relates to an edible composition comprising microbes selected from bacteria, fungi or any fragment or spore thereof for use as a vaccine in preventing a microbial disease or infection in an insect.

The present invention also relates to bacteria, fungi, any fragment thereof or any spore thereof for oral use in preventing a microbial disease or infection of an insect.

Also, the present invention relates to a method of preventing a microbial disease or infection of an insect, wherein the method comprises feeding the insect with an edible composition comprising bacteria, fungi or any fragment or spore thereof, wherein said edible composition acts as a vaccine against said microbial disease or infection.

Furthermore, the present invention relates to use of bacteria, fungi or any fragment or spore thereof in an edible composition against a microbial disease or infection of an insect.

Still, the present invention relates to an edible vaccine composition for insects, wherein the composition comprises bacteria, fungi or any fragments or spores thereof.

And still further, the present invention relates to artificial insect diet comprising bacteria, fungi or any fragment or any spore thereof or an edible vaccine composition comprising bacteria, fungi or any fragments or spores thereof.

And still furthermore, the present invention relates to a vaccine for insects, wherein the vaccine consists of bacteria, fungi, any fragments thereof and/or any spores thereof and optionally water.

Also, the present invention relates to use of bacteria, fungi, any fragments thereof and/or any spores thereof, or an edible composition comprising microbes selected from bacteria, fungi or any fragment or spore thereof, in the manufacture of a medicament for preventing microbial disease or infection.

And still, the present invention relates to an insect vaccinated with the edible vaccine composition of the present invention.

BRIEF DESCRIPTION OF THE DRAWINGS

In the following the invention will be described in greater detail by means of preferred embodiments with reference to the attached drawings, in which FIG. 1 reveals that honey bee vitellogenin (Vg) binding to bacteria was tested by western blotting (A) and microscopy (B). Binding to candidate pathogenic molecules was further tested by surface plasmon resonance technique (C). (A) Vg-rich honey bee hemolymph (hl), Vg-rich fat body protein extract (fb), or bovine serum albumin control (BSA) were incubated with *P. larvae* or *E. coli*, after which the bacteria were washed and blotted using an antibody that detects Vg or BSA. Untreated control samples are indicated (hl, fb and BSA), and next to them are located the bacteria-incubated test samples (N=3) marked with an overhead line. Two negative controls are numbered: 1=Control for Vg aggregation (fb without bacteria), and 2=control for unspecific antibody binding to *P. larvae* (above) or *E. coli* (below). The image exposure time for the *P. larvae* blot was 1 s, and 5 s for the *E. coli* blot to better reveal its weaker bands. Vg appears as a double band of 180 and 150 kDa. (B) Representative images of *P. larvae* and *E. coli* that were incubated with hemolymph, and carefully washed and fixed (N=3). The bacteria were visualized using propidium iodide (PI; red). Vg was detected using an Alexa fluor 488 nm conjugated secondary antibody (green). The primary antibody was omitted in the secondary antibody control. (C) PG (peptidoglycan), LPS (lipopolysaccharide) and zymosan, that are parts of microbial cell walls binding to Vg immobilized on a surface plasmon resonance chip. The data are blank subtracted. Above: The X-axis shows the analyte concentration, and the Y-axis shows the binding response. The curves were fitted based on five measurements at different analyte concentrations. The dots mark the binding response at each concentration measurement point. Below: The sensogram data of the maximal concentration for each analyte.

FIG. 2 shows the localization of bacterial fragments in honey bee queen ovaries in the presence (left) and absence (right) of pure Vg. Freshly detached ovaries were incubated in buffer containing fluorescent (Texas red) *E. coli* fragments, and imaged right after (A) or embedded for cryo-sectioning and imaging later (B-C). (A) Whole ovaries mounted and imaged immediately after incubation and washing steps. 5× magnification, the scale is 200 μm. (B) Eggs in cryo-sectioned ovaries. 10× magnification, the scale is 200 μm. (C) A single egg in a cryo-sectioned ovary; 20× magnification, the scale is 50 μm. In the Vg-incubated ovaries, eggs with internalized fluorescent material were observed. In the control (right), the bacterial fragments were, typically, found as bright aggregates on the membranes surrounding the eggs. The images represent N=6 queens.

FIG. 3 shows the localization of fluorescently-labeled bacterial fragments in cryo-sectioned honey bee queen ovaries incubated in the presence of pure Vg, in the presence of hemolymph proteins other than Vg, and in the absence of any externally provided protein. (A) One ovary was incubated with Vg (left) and the other with other hemolymph proteins (right), N=3. (B) One ovary was incubated with Vg (left) and the other without any protein (right), N=3. (C) One ovary was incubated without any protein (left) and the other with other hemolymph proteins but Vg (right), N=2. The scale is 50 μm, or 200 μm (the latter is indicated with scale bars).

FIG. 4 shows chromatographic fractioning of honey bee hemolymph to Vg and other proteins. S=size standard. (A) An SDS-PAGE gel with a honey bee hemolymph sample used for protein fractioning. The major proteins are (in size order) apolipophorin, vitellogenin and hexamerins. (B) Pure vitellogenin and other hemolymph proteins produced by ion-exchange chromatography. The faint ~150 and ~40 kDa bands in the pure vitellogenin fraction are the previously mass-spectrometrically verified vitellogenin fragmentation products [33]. (C) Hemolymph fractioning chromatogram. The X-axis shows the time with 0.5 ml/min flow rate, and the Y-axis shows the percentage of 0.45 M NaCl phosphate buffer. The fraction collected as pure Vg is highlighted grey. The other protein fraction collected is indicated below the X-axis.

FIG. 5 shows a table listing examples of bacteria infecting insects (Modified from Vallet-Gely et al. 2008, Nature Reviews Microbiology 6, 302-313).

FIG. 6 shows a table listing examples of bacteria infecting silk moths (silkworms) (Modified from Table 12.1. James R R and Li Z in Chapter 12 of Insect pathology (Vega F and Kaya H, Published: February 2012, ISBN: 978-0-12-384984-7)).

FIG. 7 shows a table listing examples of bacteria infecting bees (Modified from Table 12.2. James R R and Li Z in Chapter 12 of Insect pathology, Vega F and Kaya H, Published: February 2012, ISBN: 978-0-12-384984-7)).

FIG. 8 shows a table listing examples of fungi infecting silk moths (silkworms) (Modified from Table 12.1. James R R and Li Z in Chapter 12 of Insect pathology (Vega F and Kaya H, Published: February 2012, ISBN: 978-0-12-384984-7)).

FIG. 9 shows a table listing examples of fungi infecting bees (Modified from Table 12.2. James R R and Li Z in Chapter 12 of Insect pathology, Vega F and Kaya H, Published: February 2012, ISBN: 978-0-12-384984-7)).

Figure 10:
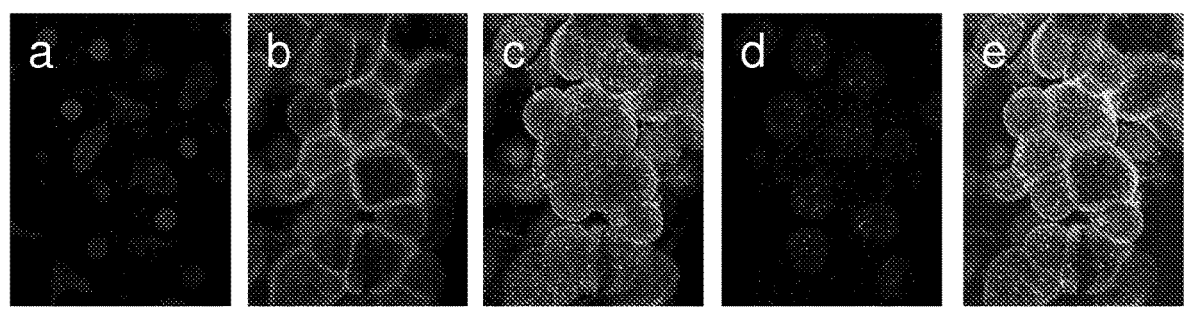

FIG. 10 shows vaccine in the fat body of the honey bee worker. FIG. 10 reveals co-localization of Vitellogenin and vaccine analogue (pieces of bacteria—*E. coli*) in the fat body of worker bees after feeding on 30% sugar solution containing Texas Red labelled *E. coli*. a)—DAPI stained cell nuclei, b)—phalloidin stained cell cytoskeleton, c)—FITC stained Vitellogenin protein, d)—Vaccine analogue (Texas Red labelled *E. coli* fragments), e)—overlay to trace co-localization of vaccine and vitellogenin.

DETAILED DESCRIPTION OF THE INVENTION

Insects

According to the present invention bacteria, fungi, bacterial fragments, fungal fragments, bacterial spores and/or fungal spores may be used for immunizing any insects which may be infected with said microbial pathogens. As used herein "insects" are a class of invertebrates within the arthropod phylum that have a chitinous exoskeleton, a three-part body (head, thorax and abdomen), three pairs of jointed legs, compound eyes and one pair of antennae. Insect refers to any stage of an insect, e.g. including but not limited to an egg, embryo, larva, pupa, adult or imago. Most specifically the insect is in the form of larva or adult. In a specific embodiment the insect is a queen. In a specific embodiment of the invention the insect is selected from the group consisting of Lepidoptera (moths and butterflies), Diptera (flies and mosquitoes), Coleoptera (beetles) and Hymenoptera (wasps, bees, ants and sawflies). In a very specific embodiment the insect belongs to Hymenoptera.

In another specific embodiment of the invention the insect is a pollinator. Pollinators move pollen from the male anthers of a flower to the female stigma of a flower to accomplish fertilization of the female gametes in the ovule of the flower by the male gametes from the pollen grain. Insect pollinators include but are not limited to bees (e.g. honey bees), wasps, among others pollen wasps (Masarinae), ants, flies including but not limited to bee flies, blue bottle flies and hoverflies, midges, mosquitoes, lepidopterans (butterflies and moths) and beetles, among others flower beetles.

In a specific embodiment of the invention the insects (e.g. insect pollinators) belong to the Order of Hymenoptera, Suborder Apocrita or Symphyta, with special attention, but not limited to all the species belonging to Superfamily of Aculeata or Parasitica. An edible composition or microbes of the present disclosure can be specifically, but not exclusively targeted for insects in the Superfamily of Apoidea, species belonging to Subgroups of Spechiformes or Anthophila, Families Andrenidae, Apidae, Colletidae, Dasypoidae, Halictidae, Megachilidae, Meganomiidae, Melittidae or Stenotritidae. In one embodiment of the invention the insect pollinators are bees. As used herein "bees" refers to any bees belonging to family Andrenidae, Apidae, Colletidae, Dasypodaidae, Halictidae, Megachilidae, Meganomiidae, Melittidae or Stenotritidae. In one embodiment of the invention the insect is a bee selected from the group consisting of eusocial bees, subsocial bees, quasisocial bees, semisocial bees, parasocial bees, solitary bees, honey bees, stingless bees, bumblebees, carpenter bees, hornfaced bees, orchid bees, orchard mason bees, leafcutter bees, sweat bees, mason bees, polyester bees, squash bees, dwarf carpenter bees, alkali bees, digger bees and allodapine bees.

As used herein stingless bees refers to bees, which cannot sting. Stingless bees include but are not limited to bees of tribe Meliponini or family Andrenidae. Meliponines have stingers, but they are highly reduced and cannot be used for defense.

As used herein "bumblebees" refer to bees that are members of the bee genus *Bombus*, in the family Apidae.

As used herein "a honey bee" is any bee, which is a member of the genus *Apis*, primarily distinguished by the production and storage of honey and the construction of perennial, colonial nests from wax. For example two species of honey bees, namely *A. mellifera* or *A. cerana indica*, are often maintained by beekeepers. Honey bees include but are not limited to *Apis andreniformis* and *Apis florea* in subgenus *Micrapis*, *Apis dorsata* in subgenus *Megapis*, and *Apis cerana*, *Apis koschevnikovi*, *Apis mellifera* and *Apis nigrocincta* in subgenus *Apis*.

In a very specific embodiment of the invention, the insect is selected from the group consisting of honey bees, bumblebees, wax moths and silk moths.

As used herein "silk moth" refers to a lepidopteran, a moth, whose caterpillar is able to produce silk. In a specific embodiment a silk moth refers to *Bombyx mori*.

Entomopathogenic Bacteria

Bacteria that infect insects are called Entomopathogenic bacteria. As used herein "bacteria" or "bacterial" refer to prokaryotic microorganisms, which are about one-tenth the size of eukaryotic cells and are typically 0.5-5.0 micrometers in length. The bacterial cell is surrounded by a cell membrane (also known as a lipid, cytoplasmic or plasma membrane). Bacteria do not usually have membrane-bound organelles in their cytoplasm, and thus contain few large intracellular structures. They lack a true nucleus, mitochondria, chloroplasts and the other organelles present in eukaryotic cells. Bacteria may be either gram positive or gram negative bacteria. In one embodiment of the invention one or more bacteria or fragments or spores thereof used for preventing a microbial disease or infection may be selected from the group consisting of *Spiroplasma* spp. (e.g. *S. apis, S. mellifera*), *Streptococcus* spp., *Staphylococcus* spp., *Enterococcus* spp. (e.g. *E. faecalis, E. faecium*), *Aeromonas* sp. (e.g. *A. mundii*), *Bacillus* spp. (e.g. *B. bombiseptieus, B. thuringiensis*), *Klebsiella* spp., *Alcaligenes* spp., *Psedomonas* spp. or any bacteria listed in a table of FIG. 5, table of FIG. 6 or table of FIG. 7.

In a more specific embodiment of the invention, one or more bacteria or fragments or spores thereof are selected from the group consisting of *Paenibacillus larvae, Melissococcus plutonius, Spiroplasma apis, Spiroplasma mellifera, Enterococcus faecalis, Enterococcus faecium, Bacillus bombyseptieus, Serratia marcescens, Aeromonas mundii* and *Bacillus thuringiensis* (e.g. subsp. *sotto*).

As used herein "microbial disease or infection" refers to any disease or infection caused by a microbe, i.e. a single cell organism including but not limited to bacteria, archaea, fungi, protists and viruses. In one embodiment of the invention the microbial disease or infection is caused by bacteria.

Foulbrood is one of the common diseases of bees, e.g. honey bees. Foulbrood may be American foulbrood (AFB) or the milder European foulbrood. American foulbrood (AFB), caused by the spore-forming *Paenibacillus larvae*, is the most widespread and destructive of the bee brood diseases. *P. larvae* is a rod-shaped bacterium. Bee larvae up to three days old become infected by ingesting spores present in their food. Young larvae less than 24 hours old are most susceptible to infection. Spores germinate in the gut of the larva and the vegetative bacteria begin to grow, taking nourishment from the larva. Spores will not germinate in larvae over three days old. Infected larvae normally die after their cell is sealed. The vegetative form of the bacterium will die, but not before it produces many millions of spores. American foulbrood spores are extremely resistant to desiccation and can remain viable for more than 40 years in honey and beekeeping equipment. *P. larvae* is highly infectious and deadly to bee brood. (See e.g. the table of FIG. 7)

European foulbrood is caused by *Melissococcus plutonius*, a bacterium that infects the midgut of the bee (e.g. honey bee) larvae. European foulbrood is considered less serious than American foulbrood. *M. plutonius* is not a spore-forming bacterium, but bacterial cells can survive several months on wax foundation. Symptoms include dead. (See e.g. the table of FIG. 7)

May disease of bees is caused by *Spiroplasma* spp. *S. apis* causes May disease in honey bees. The disease affects adults and causes quivering and inability to fly, moribund, or dead. Large numbers of infected adults may die in 4-5 weeks. (See e.g. the table of FIG. 7)

In addition to bees other insects are also susceptible to a wide range of pathogens. A disease of insect larvae called Sotto disease or Schlaffsucht is caused by *B. thuringiensis* bacteria. Upon sporulation, *B. thuringiensis* forms crystals of proteinaceous insecticidal δ-endotoxins (called crystal proteins or Cry proteins), which are encoded by cry genes. Cry toxins have specific activities against insect species of the orders Lepidoptera (moths and butterflies), Diptera (flies and mosquitoes), Coleoptera (beetles) and Hymenoptera (wasps, bees, ants and sawflies). When insects ingest toxin crystals, their alkaline digestive tracts denature the insoluble crystals, making them soluble and thus amenable to being activated with proteases expressed in the insect gut, which liberate the toxin from the crystal. The Cry toxin is then inserted into the insect gut cell membrane, perforating the digestive tract and forming a pore. As a result the insect stops eating and starves to death. Silkworms are very susceptible to these toxins. (See e.g. the table of FIG. 6)

Bacteria that cause septicemia (a morbid condition caused by the multiplication of microorganisms in the blood) e.g. in silkworms belong to many taxa. The most common bacteria include *Bacillus bombyseptieous, Serratia marcescens, Aeromonas mundii, Streptococcus* spp. and *Staphylococcus* spp. (See e.g. the table of FIG. 6).

*Enterococcus* spp. bacteria belong to intestinal bacterial species in humans and farm animals, but are not limited to these hosts. *Enterococcus* spp. are found in the farm animal and human wastes, as well as in the manure used for fertilization of the crops. They interact with many organisms and have negative effects on the environment. Said bacteria typically contaminate water supplies that can lead to infected plants as well as infections in people and animals. Insects, such as flies, can transmit the bacteria from the manure of animals and other decaying organic substrates to residential settings. E.g. in silk moth *Enterococcus* (e.g. *E. faecalis* or *E. faecium*) causes non-uniform development of larvae. Larvae become thin and small and have diarrhea. (See e.g. the table of FIG. 6)

In a specific embodiment of the invention, the microbial disease or infection is a bacterial disease or infection selected from the group consisting of *Bacillus* spp. (e.g. causing Fuliginosa septicemia), *Serratia* spp. (e.g. causing Serratia-type septicemia), *Aeromonas* spp. (e.g. causing Green thorax septicemia), *Bacillus thuringiensis* strains (e.g. causing Sotto disease or Schlaffsucht), *Enterococcus* spp. (e.g. causing bacterial flacherie, thoracic or wrinkling disease), *Paenibacillus* spp. (e.g. among others *P. larvae*, causing American foulbrood), *Melissococcus* spp. (e.g. among others *M. pluton*, causing European foulbrood), *Spiroplasma* spp. (e.g. among others *S. apis*, causing May disease) disease or infection and any other bacterial diseases. In another embodiment the microbial disease or infection is a bacterial disease or infection selected from the group consisting of *Bacillus* spp. (e.g. causing Fuliginosa septicemia), *Aeromonas* spp. (e.g. causing Green thorax septicemia), *Bacillus thuringiensis* strains (e.g. causing Sotto disease or Schlaffsucht), *Enterococcus* spp. (e.g. causing bacterial flacherie, thoracic or wrinkling disease), *Paenibacillus* spp. (e.g. among others *P. larvae*, causing American foulbrood), *Melissococcus* spp. (e.g. among others *M. pluton*, causing European foulbrood), *Spiroplasma* spp. (e.g. among others *S. apis*, causing May disease) disease or infection and any other bacterial diseases. In a very specific embodiment the microbial disease is American or European foulbrood.

In a specific embodiment of the invention specific bacteria or fragments or spores thereof are fed to insects for preventing diseases or infections caused by said specific bacteria (or fragments or spores thereof).

Entomopathogenic Fungi

Fungi that infect insects are called entomopathogenic fungi. As used herein "fungal", "fungus" and "fungi" refer to yeast and filamentous fungi i.e. moulds. In one embodiment of the invention the fungi or fragments or spores thereof used for preventing a microbial disease may be selected from Table 1 (below). The entomopathogenic fungi include Taxa from several of the main fungal groups and do not form a monophyletic group. Entomopathogenic fungi belong to the Phyla Oomycota (fungi that have cellulose in their coenocytic hyphae, without chitin and biflagellate zoospores), Chytridiomycota (groups that are without cellulose and contain chitin walls), Zygomycota (have hyphae that are multicellular, non-septate, and zygospores by the joining of gametangia), Ascomycota, Deuteromycota and Basidiomycota. Many common and/or important entomopathogenic fungi are in the order Hypocreales of the Ascomycota: the asexual (anamorph) phases *Beauveria, Metarhizium, Nomuraea, Paecilomyces=Isaria, Hirsutella* and the sexual (teleomorph) state *Cordyceps*; others (*Entomophthora, Zoophthora, Pandora, Entomophaga*) belong in the order Entomophthorales of the Zygomycota.

TABLE 1

Classification of entomopathogenic fungi
(does not include all entomopathogenic genera).

Kingdom: Protoctista
  Phylum: Oomycota
    Class: Oomycetes
      Order: Lagenidiales
        Genus: *Lagenidium*
      Order: Saproleginales
        Genus:
          *Aphanomycopsis*
          *Atkinsiella*
          *Couchia*
          *Leptolegina*
Phylum: Cytridiomycota
  Class: Cytridoimycotes
    Order: Blastocladiales
      Genus: *Catenaria*
        *Coelomomyces*
        *Coelomycidium*

TABLE 1-continued

Classification of entomopathogenic fungi
(does not include all entomopathogenic genera).

Order: Chytridiales
    Genus: *Myriophagus*
Kingdom: Mychota
Phylum: Zygomycota
  Class: Zygomycetes
    Order: Entomophthorales
      Genus: *Basidiobolus*
        *Conidiobolus*
        *Entomophaga*
        *Erynia*
        *Massospora*
        *Neozygites*
        *Strongwellsea*
        *Zoophthora*
    Order: Mucorales
      Genus: *Sporodiniella*
  Class: Trichomycetes
    Order: Amoebidiales
      Genus: *Amoebidium*
    Order: Asellariales
    Order: Eccrinales
    Order: Harpellales
Phylum: Basidiomycota
  Class: Phragmobasidiomycetes
    Order: Septobasidiales
      Genus: *Septobasidium*
        *Uredinella*
Phylum: Ascomycota
  Class: Laboulbeniomycetes
    Order: Laboubeniales
      Genus: *Hesperomyces*
  Class: Hemiascomycetes
    Order: Endomycetales
      Genus: *Candida*
        *Metchnikowia*
  Class: Loculascomycetes
    Order: Myringiales
      Genus: *Myriangium*
    Order: Pleosporales
      Genus: *Podonectria*
  Class: Plectomycetes
    Order: Ascosphaerales
      Genus: *Ascosphaera*
  Class: Pyrenomycetes
    Order: Sphaeriales
      Genus: *Calonectria*
        *Cordyceps*
        *Cordycepioideus*
        *Hypocrella*
        *Nectria*
        *Torrubiella*
Phylum: Deuteromycota
  Class: Coelomycetes
    Order: Sphaeropsidles
      Genus: *Aschersonia*
        *Tetranacrium*
  Class: Hyphomycetes
    Order: Moniliales
      Genus: *Acremonium*
        *Akanthomyces*
        *Aspergillus*
        *Beauveria*
        *Culicinomyces*
        *Engyodontium*
        *Funicularis*
        *Fusarium*
        *Gibellula*
        *Harpographium*
        *Hirsutella*
        *Hymenostilbe*
        *Metarhizium*
        *Nomuraea*
        *Paecilomyces*
        *Sorosporella*
        *Sporothrix*
        *Stibella*
        *Syngliocladium*
        *Tertacrium*
        *Tolypocladium*
        *Verticillium*
    Order: Mycelia sterlia
      Genus: *Aegerita*

In a more specific embodiment of the invention, one or more fungi or fragments or spores thereof are selected from the group consisting of *Beauveria* spp. (e.g. *Beauveria bassiana*), *Isaria* spp. (e.g. *I. javanica, I. farinosa, I. fumosoroseus*), *Hirsutella* ssp. (e.g. *H. necatrix*), *Fusarium* spp., *Nomuraea* spp. (e.g. *N. rileyi*), *Aspergillus* spp. (e.g. *A. flavus, A. ochraceus, A. oryzae, A. parasiticus, A. tamarii, A. fumigatus, A. niger*), *Nosema* (e.g. *N. apis, N. ceranae, N. bombycis, N. bombi*), *Vairimorpha* spp., *Pleisthora* spp., *Thelohania* spp, *Metarhizium* spp. (e.g. *M. anisopliae*), *Ascospaera* spp. (e.g. *A. apis, A. aggregata, A. torchioi*). This group includes e.g. filamentous and microsporidia fungi. (See e.g. tables of FIGS. 8 and 9).

In one embodiment of the invention the microbial disease or infection is caused by fungi.

The most common fungal disease of bees is chalkbrood, which occurs in the larvae. Chalkbrood is caused by fungi in the genus *Ascosphaera*, and it affects many different taxa of bees. Indeed, *Ascosphaera* spp. are found associated with bees as diverse as for example *A. mellifera, Megachile rotundata, M. centuncularis, Osmia lignaria, O. cornifrons, Trigona carbonaria*, and *Chalicodoma* spp. *A. apis* causes chalkbrood disease in honeybees. Infected larvae die at a late stage; sometimes after the cell is capped. The dead larvae are hard, chalk-white, but often mottled with black spots (the fungal spores). (See e.g. the table of FIG. 9)

Stonebrood is a fungal disease caused by *Aspergillus* spp. (e.g. *A. fumigatus, Aspergillus flavus, Aspergillus niger*). It causes mummification of the brood of a bee colony. The fungi are common soil inhabitants and are also pathogenic to other insects. The spores of the different species have different colours and when a bee larva takes in spores, they may hatch in the gut, growing rapidly to form a collar-like ring near the head. Stonebrood causes death of larvae. (See e.g. the table of FIG. 9)

Nosema diseases (dysentery or nosema disease) are caused by microsporidia in the genus *Nosema*. Transmission of these pathogens occurs when bees ingest the spores, probably in contaminated water, pollen or honey. The main effects of these pathogens include increased bee mortality and decreased colony vigor. (See e.g. the table of FIG. 9)

The muscardines are fungal diseases and are common silkworm diseases in China and Japan. The muscardine fungi produce asexual infective spores. Depending on the pathogen species, these spores are white, green, yellow, black, grey or red, and the muscardine diseases are named based on these colors (e.g. *Metarhizium anisopliae* causes black and *Nomuraea rileyi* green muscardine). Muscadines cause death of larvae. (See e.g. the table of FIG. 8) In addition to fungi causing muscardines mentioned in FIG. 8 other fungi include e.g. *Isaria javanica* (grey muscardine), *Isaria farinose* (yellow muscardine), *Isaria fumosoroseus* (red muscardine) and *Hirsutella* ssp. (e.g. *H. necatrix*) (grassy muscardine).

Diseases caused by *Aspergillus* spp. are called aspergillosis. For example silkworms cadavers with aspergillosis become stiff and mycelia emerge from the integument. The fungi causing this disease in silkworms include more than ten *Aspergillus* species. The fungus kills the instars in two to six days. (See e.g. the table of FIG. 8)

*Fusarium* species cause fusariosis in silk moths. Fusariosis is characterized by a fecal mass on the anus premortem and postmortem.

Pebrine is caused in moths by various microsporidia e.g. by *Nosema bombycis* as well as *Vairimorpha, Pleisthora* or *Thelohania* species. Pebrine causes death of larvae and infected adult moths have deformed wings and distorted antennae. Adults with pebrine mate poorly and have poor egg production. (See e.g. the table of FIG. 8)

In a specific embodiment of the invention, the microbial disease or infection is a fungal disease or infection selected from the group consisting of chalkbrood, stonebrood, dysentery, nosema disease, muscardine, aspergillosis, fusariosis, pebrine, *Beauveria* spp. (e.g. *Beauveria bassiana*) infection, *Isaria* spp. (e.g. *I. javanica, I. farinosa, I. fumosoroseus*) infection, *Hirsutella* ssp. (e.g. *H. necatrix*) infection, *Fusarium* spp. (e.g. *F. verticillioides*) infection, *Nomuraea* spp. (e.g. *N. rileyi*) infection, *Aspergillus* spp. (e.g. *A. flavus, A. ochraceus, A. oryzae, A. parasiticus, A. tamarii, A. fumigatus, A. niger*) infection, *Nosema* spp. (e.g. *N. apis, N. ceranae, N. bombycis, N. bombi*) infection, *Vairimorpha* spp. (e.g. *V. ephestiae*) infection, *Pleisthora* spp. infection, *Thelohania* spp. (e.g. *T. solenopsae*) infection, *Metarhizium* spp. (e.g. *M. anisopliae*) infection and *Ascospaera* spp. (e.g. *A. apis, A. aggregata, A. torchioi*) infection. In another embodiment the microbial disease or infection is a fungal disease or infection selected from the group consisting of chalkbrood, stonebrood, dysentery, muscardine, aspergillosis, fusariosis, pebrine, *Beauveria* spp. (e.g. *Beauveria bassiana*) infection, *Isaria* spp. (e.g. *I. javanica, I. farinosa, I. fumosoroseus*) infection, *Hirsutella* ssp. (e.g. *H. necatrix*) infection, *Fusarium* spp. (e.g. *F. verticillioides*) infection, *Nomuraea* spp. (e.g. *N. rileyi*) infection, *Aspergillus* spp. (e.g. *A. flavus, A. ochraceus, A. oryzae, A. parasiticus, A. tamarii, A. fumigatus, A. niger*) infection, *Vairimorpha* spp. (e.g. *V. ephestiae*) infection, *Pleisthora* spp. infection, *Thelohania* spp. (e.g. *T. solenopsae*) infection, *Metarhizium* spp. (e.g. *M. anisopliae*) infection and *Ascospaera* spp. (e.g. *A. apis, A. aggregata, A. torchioi*) infection.

In a specific embodiment of the invention specific fungi or fragments or spores thereof are fed to insects for preventing diseases or infections caused by said specific fungi (or fragments or spores thereof).

Compositions and Artificial Diets

The present invention relates to compositions and insect artificial diets comprising bacteria, fungi, fragments and/or spores thereof. Also, the present invention relates to bacteria, fungi, fragments and/or spores thereof as such for preventing insect diseases. Most specifically, the composition or insect artificial diet of the invention comprises bacteria, fragments and/or spores thereof.

As used herein, an "insect artificial diet" refers to diet, which is fed to insects and which does not occur in nature as such but is artificially prepared by methods well known to a person skilled in the art. As used herein "artificially prepared" refers to a mixture of specific macronutrients (e.g. carbohydrates, proteins and/or fatty acids) with optionally added micronutrients (e.g. various minerals, salts and/or nucleic acids) as well as optional water. Different artificial diets have been developed to mimic the natural diet and to take into account specific requirements of specific insect species for nutrients. In some embodiments artificial diet may or may not comprise plant or animal material. As it is clear to a person skilled in the art natural insect diet cannot always be fed, e.g. in the lab, for practical and economical reasons (e.g. insects need a lot of plant tissue for several weeks to complete their development and it would not be feasible to grow plants in this amounts in the greenhouses or pollinators need sugary floral nectar, what would require a lot of flowering plants in containment).

The exact composition of the macro- and/or micronutrients depends on the insect species. The diet ingredients may be commercial or from the relevant vendor and mixed according to the recipes well known to a person skilled in the art. As agar is often used to solidify the diet mixture, the dry ingredients may be optionally mixed with added water and optionally heated up on the heated plate or in the microwave. After allowing the diet to cool to the room temperature it may optionally be portioned and thereafter fed to the insects.

In one embodiment of the invention, in addition to bacteria, fungi or fragments or spores thereof and optional water, the insect artificial diet further comprises sugar (e.g. in the case of honey bee artificial diet). In one embodiment the sugar is in the form of sugar solution or paste. As used herein "sugar" refers to a sweet, short-chain and soluble carbohydrate. Sugar may be selected e.g. from the group consisting of monosaccharides, disaccharides and oligosaccharides, more specifically glucose, fructose, galactose, sucrose, fructose, glucose, maltose, lactose, cane sugar, beet sugar, and isomerized corn syrup. The sugar for use in the present invention may specifically be sucrose, but any formulation which is functionally and/or chemically mimetic of nectar may be employed. In one embodiment the sugar solution is water solution. Particularly specific are 50% w/v sucrose solutions. In a specific embodiment of the invention the amount of sugar in the composition or artificial insect diet of the invention is 10-95%, 20-95%, 30-95%, 40-95%, more specifically 50-95%, more specifically 60-90%, more specifically 70-90% and more specifically 75-85%, or e.g. 90%, 91%, 92%, 93%, 94%, 95%, 96%, 97%, 98% or 99% by weight.

The majority of honey bee larvae eat honey, but larvae that are chosen to become future queens will be fed with royal jelly. In a specific embodiment, the artificial diet comprises royal jelly. Royal jelly is a white secretion produced by young, female worker bees. It is comprised of pollen and chemicals from the glands of worker bees. Royal jelly contains dietary supplements, fertility stimulants and other medicines, as well as B vitamins. Workers and drones are fed royal jelly during the first few days of larval development, while future queen larvae consume royal jelly throughout their development. The edible composition of the present invention may be mixed with at least any natural or artificial insect food including but not limited to any of those mentioned in this disclosure (e.g. honey, pollen, water). In a specific embodiment of the invention the amount of royal jelly in the composition or artificial insect diet of the invention is 40-95%, more specifically 50-95%, more specifically 60-90%, more specifically 70-90% and more specifically 75-85% by weight.

In one embodiment of the invention the insect artificial diet is implemented with amino acids. One or more amino acids may be selected from the group consisting of alanine, arginine, asparagine, aspartic acid, cysteine, glutamic acid, glutamine, glycine, pyrrolysine, proline, selenocysteine, serine, histidine, isoleucine, leucine, lysine, methionine, phenylalanine, threonine, tryptophan and valine.

In addition to bacteria, fungi or fragments or spores and optional sugar and/or optional amino acids and/or optional royal jelly, the insect artificial diet of the invention may further comprise (depending on the insect to be vaccinated), but is not limited to, one or more from the group consisting of wheat germ, Wess Salt mix, agar, methyl parabene, ascorbic acid, cellulose, pinto bean flour, soy bean flour, wheat flower, mulberry leaves powder, dried plant parts (e.g. leaves, stems, roots and/or flowers), yeast extract, brewer's yeast products and tapioca flour. Artificial diet may also optionally include protein, carbohydrate or pollen supplemental foods, any dry mixes, moist cakes, candy patties, sugar syrups, sugar candies, and dry sugar. As an example the common insect diet for herbivorous Lepidopteran larvae may comprise, but is not limited to, Pinto bean, Torula yeast, Wheat germ, Ascorbic acid, Methyl p-nydroxybenzoate, Sorbic acid, Formaldehyde 10%, Water, and/or Agar.

Some specific examples of the insect artificial diet comprising vaccine compositions are shown in the examples of the present disclosure.

In one embodiment of the invention, the amount of bacteria, fungi, any fragment and/or spore thereof in the composition (e.g. edible composition) or artificial insect diet of the present invention is from 1 to 100%, 1 to 90%, 1 to 80% 1 to 70%, 1 to 60%, 1 to 50%, 1 to 40%, 1 to 30%, 1 to 20%, 1 to 10% or 1 to 5% by weight. This composition or artificial diet provides a significant prevention of microbial infections and/or diseases. In a very specific embodiment, the amount of bacteria or fragments or spores thereof in the edible composition is from 90 to 100% by weight. In another very specific embodiment the amount of bacteria or fragments or spores thereof in the insect diet is from 0.1 to 10% by weight.

In a further embodiment the amount of bacteria, fungi, any fragment and/or spore thereof is from 1 to 10% by weight (or 1-20%, 1-30%, 1-40%, 1-50%, 1-60%, 1-70%, 1-80% or 1-90% by weight) and the amount of sugar is about 80% by weight (or about 30%, 40%, 50%, 60%, 70% or 90% by weight). In a very specific embodiment, the amount of *Melissococcus pluton* or *Paenibacillus larvae* bacteria in the composition or insect diet of the present invention is from 1 to 10% by weight (or 1-20%, 1-30%, 1-40%, 1-50%, 1-60%, 1-70%, 1-80% or 1-90% by weight) and the amount of sugar is about 80% by weight (or about 30%, 40%, 50%, 60%, 70% or 90% by weight).

The amount of the bacteria, fungi or any fragment or spore thereof in the composition or diet may be adjusted depending on the properties of other agents of the composition and the type of insect administered with the composition. Need of delivering the composition to one or more dosages, and the dosage frequency per year are determined depending on the properties of the specific composition and a condition to be treated.

In a specific embodiment, bacteria, fungi or any fragment or spore thereof are the only therapeutically effective agents of the composition or the insect artificial diet. In another specific embodiment the bacteria, fungi or any fragments or spores thereof are therapeutically effective agents as such.

In one specific embodiment of the invention, the composition or insect diet comprises bacteria and/or fragments or spores thereof from one or more different types of bacteria. Therefore, the composition or insect diet may comprise at least two or at least three different types of bacteria and/or fragments or spores thereof.

In another specific embodiment of the invention, the composition or insect diet comprises fungi and/or fragments or spores thereof from one or more different types of fungi. Therefore, the composition or insect diet may comprise at least two or at least three different types of fungi and/or fragments or spores thereof.

As used herein "bacterial or fungal fragments" refer to any fragments of the bacteria or fungi, e.g. any part, piece, or polypeptide of the bacteria, or any combination thereof. Herein, the term "polypeptide" refers to polymers of amino acids of any length. In a specific embodiment the fragments may be selected from cell wall fragments or cell recognition molecules. As used herein "cell wall fragments" refer to fragments of a cell wall i.e. fragments of a structural layer surrounding a cell. E.g. in bacteria the cell wall is composed mainly of peptidoglycans and in fungi the cell wall comprises chitin and other polysaccharides. In a specific embodiment vitellogenins (Vg) bind to said bacteria, fungi and/or fragments or spores thereof, such as cell wall fragments. As used herein "cell recognition molecules" refer to molecules taking care of interaction between cells e.g. including but not limited to surface molecules or membrane glycoproteins. In a very specific embodiment of the invention microbes or fragments or spores thereof are transferred from the insect to the egg or larvae by insect lipoproteins vitellogenins (Vg).

Spores of bacteria or fungi may also be utilized in the present invention. As used herein "bacterial spore" refers to a spore or spore-like structure produced by bacteria including but not limited to endospores, Akinetes, and spores produced by Actinobacteria and *Azotobacter*. Spore formation in bacteria is a method of surviving unfavourable conditions. As used herein "fungal spores" refer microscopic biological particles that allow fungi to be reproduced i.e. fungal spores form part of the life cycles of fungi. In one embodiment of the invention the edible composition comprises bacterial endospores (optionally in combination with vegetative cells).

In a specific embodiment bacteria, fungi or fragments or spores thereof are provided in the form of washed and/or concentrated preparations. Such preparations can be prepared by any of a wide range of known microbiological techniques. Typical methods would include growth of spores or vegetative cells to stationary phase in liquid media or on agar plates followed by separation by direct centrifugation or harvesting of the cells from the agar plates followed by centrifugation.

In one embodiment of the invention the bacteria, fungi, fragments and/or spores thereof are live. In another embodiment of the invention the bacteria, fungi, fragments thereof and/or spores thereof are dead, attenuated and/or avirulent. Methods of producing or treating dead, attenuated and/or avirulent bacteria, fungi, fragments and/or spores thereof are known to a person skilled in the art and are described in various handbooks or manuals in the field. In one specific embodiment of the invention the bacteria, fungi, fragments and/or spores thereof are heat-killed e.g. at a temperature of 80-130° C. (e.g. 90° C., 105° C. or 121° C.) for 5-60 minutes (e.g. 5-20, 5-15 or 10, 20, 30, 40 or 50 minutes), optionally before or after applying them to the composition or insect diet.

The composition or artificial diet may be administered to insects one or several times a year. In a specific embodiment of the invention the composition is for administration one, two or three times a year, more specifically two times per year e.g. before hibernation and after it. The composition or artificial diet may be delivered as a single dose, or in several smaller doses administered at intervals. The composition or artificial diet may be delivered to any component of the hive, or to the insect cluster itself.

Compositions of the present invention are easily administered or fed to insects. In addition to bacteria, fungi, fragments and/or spores thereof, the edible composition may optionally comprise one or more acceptable (e.g. pharmaceutically acceptable) agents selected from the group consisting of carrier(s) (e.g. water, glucose or lactose), adjuvant(s), excipient(s), auxiliary excipient(s), antiseptic(s), stabilizing, thickening or coloring agent(s), perfume(s), binding agent(s), filling agent(s), lubricating agent(s), suspending agent(s), sweetener(s), flavoring agent(s), gelatinizer(s), anti-oxidant(s), preservative(s), buffer(s), pH regulator(s), wetting agent(s) and components normally found in corresponding products. However, in a very specific embodiment of the invention only bacteria, fungi, fragments thereof and/or spores thereof are needed in the composition. In a further specific embodiment the composition consists of only bacteria, fungi, fragments thereof and/or spores thereof and water.

In one specific embodiment of the invention, the compositions or artificial diet may be used for example in solid, semisolid or liquid form, such as in the form of patties, syrups, drenches, dustings, pastes, tablets, pellets, capsules, solutions, emulsions, suspensions or like. Preferably the composition is for oral administration.

The composition or artificial diet of the invention comprises bacteria, fungi, bacterial spores, fungal spores and/or fragments thereof in an amount sufficient to produce the desired effect. Other ingredients as well as other specific components of the compositions or artificial diet are either obtained commercially or prepared by conventional techniques known in the art. Amounts and regimens for feeding or administration of bacteria, fungi or fragments or spores thereof (e.g. in the edible composition of artificial diet) can be determined readily by those skilled in the art of preventing microbial infections of insects. Generally, the dosage of the bacteria, fungi or fragments or spores thereof will vary depending on considerations such as insect type as well as a size, stage, age, gender and general health of the insect. Also, any other therapeutically effective agents or agents having preventive effects may be utilized in the present invention. Also, other concurrent diets or compositions may be utilized in addition to the diets or compositions of the present disclosure. Frequency of feeding and nature of the effect desired as well as other variables may be adjusted by insect farmers.

In a specific embodiment of the invention the edible composition is used as the only vaccine in the insect for preventing a microbial disease or infection.

The compositions or artificial diet may be manufactured by any conventional processes known in the art. Generating the composition or artificial diet means that bacteria or fragments thereof may for example be added to any products or mixed with any agents. The bacteria or any fragment thereof may be added or mixed either in connection with the preparation of the composition or artificial diet or thereafter, during the finishing of the end product. The edible composition of the present invention may be mixed with at least any artificial insect food including but not limited to any of those mentioned in this disclosure. Mixing methods include any conventional mixing methods known to a person skilled in the art.

In a very specific embodiment, the composition or artificial diet further comprises a vitellogenin polypeptide, fragments thereof, polynucleotide encoding the vitellogenin polypeptide or fragments thereof.

Alterations of the immune response of an insect can be checked by in vitro, ex vivo or in vivo tests from any biological sample. In vivo experiments include but are not limited to the determination of a response to vaccines.

As used herein vaccination refers to administration or feeding of antigenic material (a vaccine) to stimulate an immune system against a pathogen.

As used herein, the term "prevent" or "preventing" refers to feeding or administration of microbes to an insect for purposes which include not only 100% or complete prevention but also partial prophylaxis and therefore also amelioration or alleviation of disorders or symptoms related to microbial infections. Preventive effect may be assessed e.g. by monitoring the symptoms mentioned in any of the tables of FIGS. 6-9. In this respect, the present invention can provide any amount of increase e.g. in the survival data compared to untreated controls.

It will be obvious to a person skilled in the art that, as the technology advances, the inventive concept can be implemented in various ways. The invention and its embodiments are not limited to the examples described above but may vary within the scope of the claims.

EXAMPLES

Materials and Methods
1. Production of Edible Vaccination Comprising Microbes or Fragments or Spores Thereof

*Paenibacillus larvae* genotype Eric II (strain 233/00), was acquired CCUG: Culture Collection, University of Göteborg in Sweden. The dried culture was dissolved in MYPG medium and plated out on MYPG agar plates, plates were cultivated for 7 days at 35° C. and all the bacterial cells were harvested into the 1×PBS buffer and frozen at −20° C. until further use. Two (8 cm in diameter) plates were harvested into 0.5 ml 1×PBS. Further the bacterial solution was autoclaved for 20 min at 121° C. and aliquot of it was plated out on the sterile MYPG agar to assure, that all the bacteria were dead. Prior mixing to the insect feed (here queen diet), the solution was centrifuged, where 1.5 ml of the preparation was centrifuged at 10,000 rpm for 10 min at room temperature, supernatant was removed and cells were dissolved in 100 microliters of millipore water. This preparation forms a vaccine part in the insect feed. Next the prepared mixture was added to the queen feed acquired from Imkereibedarf Uwes Bienenkorb (Königin-futterteig, #5407) to form 1% of the final mass.

A vaccine composition or insect feed comprising the vaccine composition may be produced for any insect according to this Chapter 1 of materials and methods (Production of edible vaccination comprising microbes or fragments or spores thereof). The feed to be mixed with the vaccine composition may be chosen depending on the target insect.

A vaccine composition comprising fungi or fragments or spores thereof may be produced according to similar methods as described in the above paragraphs of Chapter 1 of materials and methods (Production of edible vaccination comprising microbes or fragments or spores thereof). Furthermore, the vaccine composition is added to the insect artificial diet of interest.

1a) Description of the Food Preparation with Vaccine for Honey Bees

For creating the edible vaccine for the honey bee queens, as an example 10 grams of sugar paste (8 grams of granulated sugar, 2 grams of water) was mixed with 100 microliters of vaccine composition.

1b) Description of the Food Preparation with Vaccine for Moths

To grow larvae of the generalist herbivorous moth larvae, as an example artificial diet (casein 31.5 g, sucrose 33.76 g, wheat germ 43.76 g, Wess salt 9 g, potassium sorbate 1 g, cellulose 6.26 g, methyl paraben 1.36 g, lepidopteran vitamin mix 9 g, aureomycin 1 g, ascorbic acid 3.5 g, propyl gallate 0.2 g, 40% formaldehyde 1.5 ml, linseed oil 6.5 ml, 45% potassium hydroxide 2.5 ml, 24 g agar and 750 ml water) mixed with vaccine composition can be used.

1c) Description of the Food Preparation for Moths

In order to prepare the artificial diet for the silkworms as an example 100 g of powder (Dried mulberry leaf powder 25.0 g, Defatted soybean meal 36.0 g, Wheat meal 15.0 g, Corn starch 4.0 g, Soybean fiber 5.0 g, Citric acid 4.0 g, Ascorbic acid 2.0 g, Salt mixture 3.0 g, Agar 4.2 g, Vitamin mixture 399.0 mg, Sorbic acid 200.0 mg, Propionic acid 691.0 mg, Chloramphenicol 10.0 mg, b-sitosterol 500.0 mg) was dissolved in 2.6 g of double distilled water and mixed with 100 microliters of dead bacterial solution per 10 g of diet.

2. Insect Rearing and Treatment (*Apis mellifera*)

Single hive produced *Apis mellifera* sibling queens were acquired from the professional bee keeper. Queens were caged with 10 worker bees in the small so called queen cages and fed with prepared queen bee vaccine, consisting of 1% of autoclaved and previously frozen sterile bacterial preparation (see above under 1. Production of edible vaccination comprising bacteria or bacterial fragments) in 10 g of feed. 6 Queens were fed with vaccine for 7 days and kept in the climate cabinet at 30° C. As control 6 queens were fed with queen diet mixed with water. Vaccine was renewed every 3 days. After one week queens were transferred to the small Apidea bee hives, consisting of ca. 350 workers. Queens were allowed to settle and start to lay eggs. After 3 days hives were open and small larvae were removed and transferred to lab, where they were infected with 3 different doses of *Paenibacillus* larvae spores (10, 15 and 20 spores per larvae). Mortality was reordered.

Rearing or treatment conditions similar to *Apis mellifera* queens as described above may be utilized or modified also for other insects.

3. Western Blot with Live *P. larvae* and *E. coli* (*Apis mellifera*)

Wintertime worker honey bee hemolymph (hl) and fat body protein extract (fb) are rich in Vg, and were used for testing Vg-binding to bacteria, adapted from the fish Vg experiment by Tong et al. (Immunobiology. Elsevier; 2010; 215: 898-902) using an antibody that detects honey bee Vg. For cell-free hl and fb sampling, see Havukainen et al. (J Exp Biol. 2011; 214: 582-592). The experiment was performed at room temperature, centrifugation steps were 3,000 g for 5 min, and wash volume was 0.5 ml of PBS, if not mentioned otherwise. *P. larvae* (strain 9820 purchased from Belgian Co-ordinated Collections of Micro-organisms, Gent, Belgium) grown on MYPGP agar plates for 7 days and Epicurian Gold *E. coli* grown in LB medium liquid culture overnight were washed and suspended in 100 µl PBS per sample. The bacteria suspensions ($\sim 1.3 \times 10^8$ cells/ml) were mixed with either an equal volume of hemolymph diluted 1/10 in PBS with a protease inhibitor cocktail (Roche, Penzberg, Germany) or with fat body protein extract (5.7 mg/ml total protein in PBS with the protease inhibitors). The following negative controls were used: 1) 100 µl *P. larvae* and *E. coli* with an equal volume of PBS but no hl/fb, to detect possible unspecific antibody binding to the bacteria, 2) 100 µl fb with an equal volume of PBS, but no bacteria, to detect possible Vg aggregation, and 3) 100 µl *P. larvae* and *E. coli* treated with 100 µl 5 mg/ml bovine serum albumin (BSA; control protein). As untreated controls, we kept on ice 0.1 µl of hl, 0.5 µl of fb extract, and 1 µl of BSA. The samples were incubated at 26° C. for 50 min under agitation for Vg-bacteria binding to occur. The bacteria were washed six times. The final pellet was resuspended in 10 µl of 4 M urea in PBS, agitated for 15 min and centrifuged. The samples were blotted on a nitrocellulose membrane according to a standard horse-radish peroxidase conjugate protocol with the Vg antibody tested before (Havukainen H et al. J Exp Biol. 2011; 214: 582-592; Seehuus S-C et al. J Insect Sci. 2007; 7: 1-14) (dilution 1:25,000; Pacific Immunology, Ramona, Calif., USA), or a commercial BSA antibody (1:2000; Life Technologies, Carlsbad, Calif., USA). The bands were visualized using Immune-Star kit and ChemiDoc XRS+ imager. All blotting reagents were purchased from Bio-Rad (Hercules, Calif., USA).

4. Microscopy of *P. larvae* and *E. coli* (*Apis mellifera*)

Vg-binding to bacteria was further tested by fluorescence microscopy. The incubation with hl was as above, except hl and bacteria volumes were both 20 µl and the number of bacterial cells was $\sim 3 \times 10^6$. All centrifugation steps were 10,000 g, +4° C., 5 min and PBS-T wash volumes were 1 ml. After hl incubation with the bacteria, the bacteria were washed and fixed with 4% paraformaldehyde for 10 min in room temperature. The cells were washed twice and blocked with 5% milk in PBS-T for 30 min in room temperature and washed again. Vg primary antibody (same as above) was used 1:50 in PBS-T and 1% milk for overnight incubation at +4° C. The samples were washed twice and incubated with Alexa fluor 488 nm anti-rabbit antibody, 1:50, for 1 h in room temperature in dark and washed three times. DNA was stained with standard propidium iodide (PI) protocol (Invitrogen). The bacteria were mounted with glycerol and imaged with Zeiss Axio Imager M2, excitations 499 nm and 536 nm, and emissions 519 nm and 617 nm. The primary antibody was omitted in the treatment of the secondary antibody control samples.

5. Surface Plasmon Resonance with LPS, PG and Zymosan (*Apis mellifera*)

Vg was purified from honey bee hemolymph with ion-exchange chromatography as described before (Havukainen H et al. J Biol Chem. 2013, 288: 28369-81; Seehuus S-C et al. J Insect Sci. 2007; 7: 1-14). Biacore T200 instrument (GE Healthcare, Waukesha, USA) and buffers from the manufacturer were used. The analytes were bought from Sigma Aldrich: PG from *S. aureus* #77140, LPS from *E. coli* #L2630 and zymosan from *S. cerevisiae* #Z4250. 30 µl/ml Vg in 10 mM acetate buffer pH 4.5 was immobilized on a CM5 chip—primed and conditioned according to the manufacturer's instructions—until the response reached 5150 RU. The chip was blocked using ethanolamine. The analytes were suspended in the running buffer (0.1 M HEPES, 1.5 M NaCl and 0.5% v/v surfactant P20) and heated at 90° C. for 30 min with repeated vigorous vortexing, followed by spinning in a table centrifuge for 20 min. Zymosan was heated for an additional 30 min at 95° C. before centrifugation. PG and zymosan form a fine suspension in water solutions, and they formed a pellet during the centrifugation; their concentrations are given here as the weight added to the volume. The analytes were run with 120 s contact time and 600 s dissociation time with a 30 µl/min flow rate at 25° C. The analytes flowing in a separate channel on a naked chip was used as a blank, whose value was subtracted from the sample. After optimizing the binding-range, the following concentrations were measured. PG: 0, 0.25, 0.5, 2, 3, 5 mg/ml; LPS: 0, 0.1, 0.2, 0.9, 1.8, 3 mg/ml, and zymosan: 0, 0.5, 1, 2, 3, 4 mg/ml. PG and LPS binding did not reach binding saturation, yet, we did not exceed 5 mg/ml or 3 mg/ml concentration, respectively, to avoid analyte aggregation (see the manufacturer's information and references therein for work concentrations).

6. Microscopy of Queen Ovaries (*Apis mellifera*)

Six one year old *A. mellifera ligustica* queens were anesthetized on ice. Their ovaries were dissected and washed in ice cold PBS. One of the paired ovaries per queen was then placed in control solution (50 µl PBS containing 2 mg/ml Texas Red labeled *E. coli* Bioparticles; Life Technologies, Carlsbad, Calif., USA) and the other ovary was placed in the same solution that contained, in addition, 0.5 mg/ml Vg purified from honey bee hemolymph (Havukainen H et al. J Biol Chem. 2013, 288: 28369-81; Havukainen H et al. J Exp Biol. 2011; 214: 582-592). The ovaries were incubated at 28° C. for 2 h under agitation. Next, the ovaries were washed twice in 1 ml ice cold PBS for 5 min under agitation. Samples of two queens were directly mounted using Fluoromount (Sigma) and observed by bright field and fluorescence (excitation 595 nm, emission 615 nm) microscopy (Axio Imager M2, Carl Zeiss AG, Oberkochen, Germany). One additional untreated control queen was imaged for detection of the autofluorescent pedical area of the ovary. The remaining four queens were embedded in Tissue-Tek (Sakura Finetek, Torrance, Calif., USA) and stored in −80° C. These ovaries were cut in 17 mm sections at −20° C., and imaged immediately after mounting. The microscopy settings were kept constant during imaging.

Figure 4:
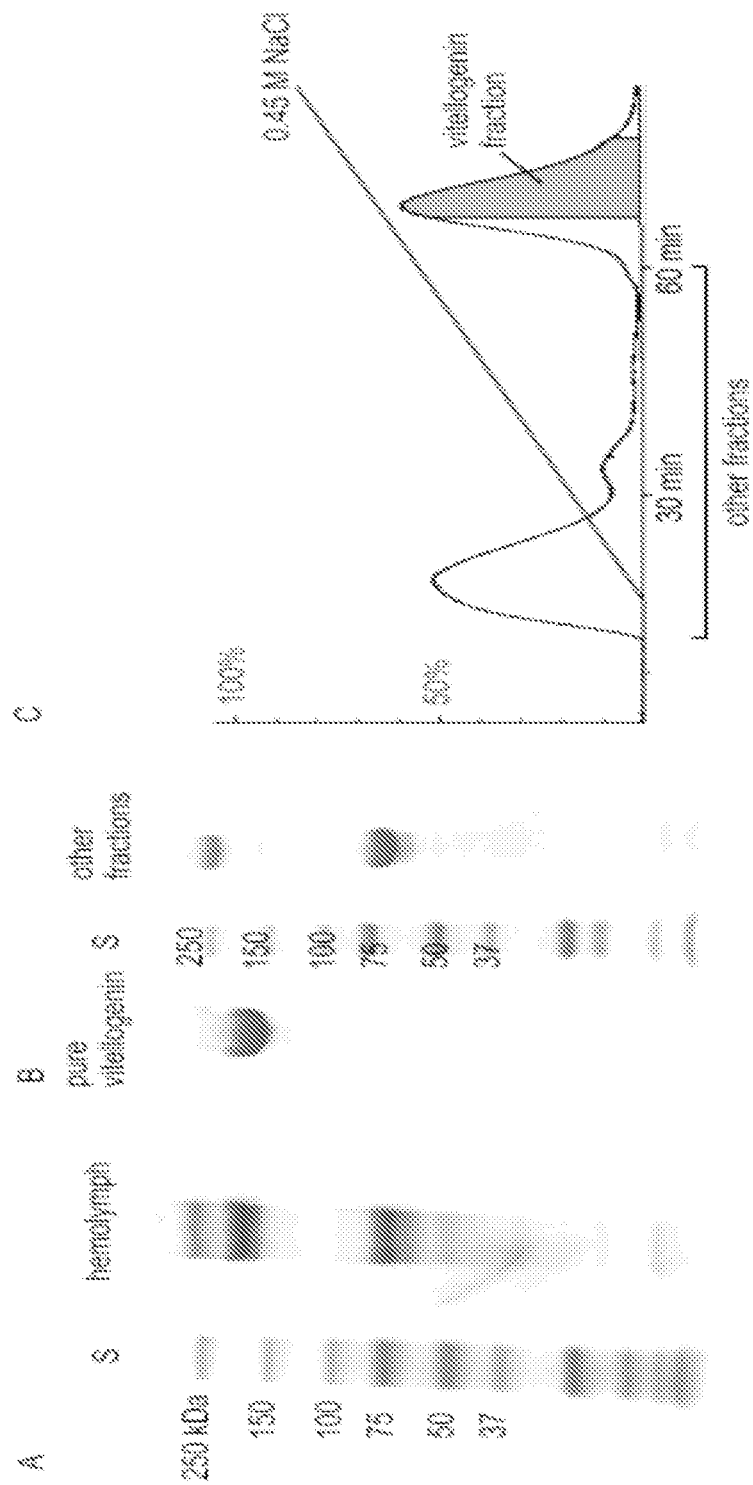

To test whether hemolymph proteins could trigger the uptake of immune elicitors even in the absence of Vg, we modified the experimental setup to include hemolymph proteins other than Vg, the majority of which are apolipophorin and hexamerins, both known to bind to immune elicitors (Wang Z et al. PLoS Pathog. 2010, 6). The other hemolymph proteins were obtained by running ion-exchange chromatography on honey bee hemolymph and dividing the collected hemolymph fractions into Vg and non-Vg proteins (FIG. 4) (Havukainen H et al. J Biol Chem. 2013, 288: 28369-81; Havukainen H et al. J Exp Biol. 2011; 214: 582-592). Remaining small molecular weight hemolymph molecules, such as possible peptides and hormones, were removed during protein concentration using centrifugal filters with 50 kDa cutoff with both Vg and non-Vg fractions (Millipore, Billerica, Mass., USA). Fractions containing both Vg and other hemolymph proteins were discarded. The Vg and the non-Vg proteins had a final concentration of 0.5 mg/ml in the experiment. The queens were as above. The setup was as follows (all incubations contained the *E. coli* Bioparticles 1.5 mg/ml): one ovary was incubated with Vg and the other ovary with control solution (see above) (N=3); one with Vg and the other with non-Vg hemolymph proteins (N=3), and one ovary with non-Vg hemolymph proteins and the other with control solution (N=2). The cryo-section imaging was done as above.

7. Vaccination of Silkworm (*Bombyx mori*) Against the Flacherie Disease Caused by *Enterococcus faecalis*

Flacherie (meaning "flaccidness", expressed as lethal diarrhea) can be caused by larvae feeding on the mulberry leaves contaminated with *Enterococcus faecalis*. *Enterococcus faecalis* is an opportunistic soil dwelling entomopathogenic bacterium with global distribution. 40 ml of sterile Luria Bertoni medium (5 g NaCl, 10 g Yeast extract, 10 g Tryptone dissolved in 1 L of double distilled water) was inoculated with a single colony of *Enterococcus faecalis* and bacteria were allowed to grow in 30° C. for 48 hours. After that bacterial cells were harvested and dissolved in 1 ml of 1×PBS and killed by autoclaving. To ensure, that all the bacteria are dead, an aliquot was plated on the Luria Bertoni agar plates (5 g NaCl, 10 g Yeast extract, 10 g Tryptone, 15 g of Agar dissolved in 1 L of double distilled water) and checked for the colony formation. As no colonies were formed in 48 h, the killing of bacteria was considered successful.

Artificial diet described in paragraph 1c) above was cooked in an autoclave for about 40 min at 105° C. The diet was cooled to room temperature and then maintained in a refrigerator (4° C.) until its utilization.

Freshly laid eggs of Silkworms were placed on the diet with vaccine and allowed to hatch and start feeding on it. Larvae were kept at 25° C. with relative humidity of 75% until pupation.

Results

1. Vg Binds to Bacteria and Pathogen Patterns

We first verified that honey bee Vg can bind to *P. larvae*—the Gram-positive bacterium that causes American foulbrood disease—and to Gram-negative *E. coli* by using western blotting and microscopy with live bacteria and an antibody that recognizes Vg (FIG. 1A-B). In the western blot, Vg signal was found in both *P. larvae* and *E. coli* samples that had been incubated with Vg-rich honey bee hemolymph or fat body homogenate and then thoroughly washed (FIG. 1A). The Vg signal appears to be stronger in the *P. larvae* samples than in the case of the *E. coli* samples. Negative controls were used to verify that the Vg signal was not due to Vg aggregation (a sample of fat body homogenate without any bacteria; lane 1, FIG. 1A) or due to unspecific antibody binding to bacteria (samples of bacteria only; lanes numbered 2, FIG. 1A). Also, bovine serum albumin (BSA) was used as a negative control, and this protein showed no binding to either bacterial species (FIG. 1A; BSA). We did fluorescence microscopy of *P. larvae* and *E. coli* incubated with honey bee hemolymph to verify the western blot result, and Vg signal was observed covering the bacteria (FIG. 1B). The antibody controls for unspecific binding showed no signal.

We then verified honey bee Vg binding to the pathogen patterns PG (predominantly a Gram-positive bacteria signature molecule), LPS (Gram-negative signature) and zymosan (yeast) using a surface plasmon resonance technique (FIG. 1C). We detected the highest binding response for PG followed by LPS, whereas the binding response to zymosan was modest.

2. Vg is Required for the Transport of Bacteria-Derived Molecules Into Eggs

Figure 2:
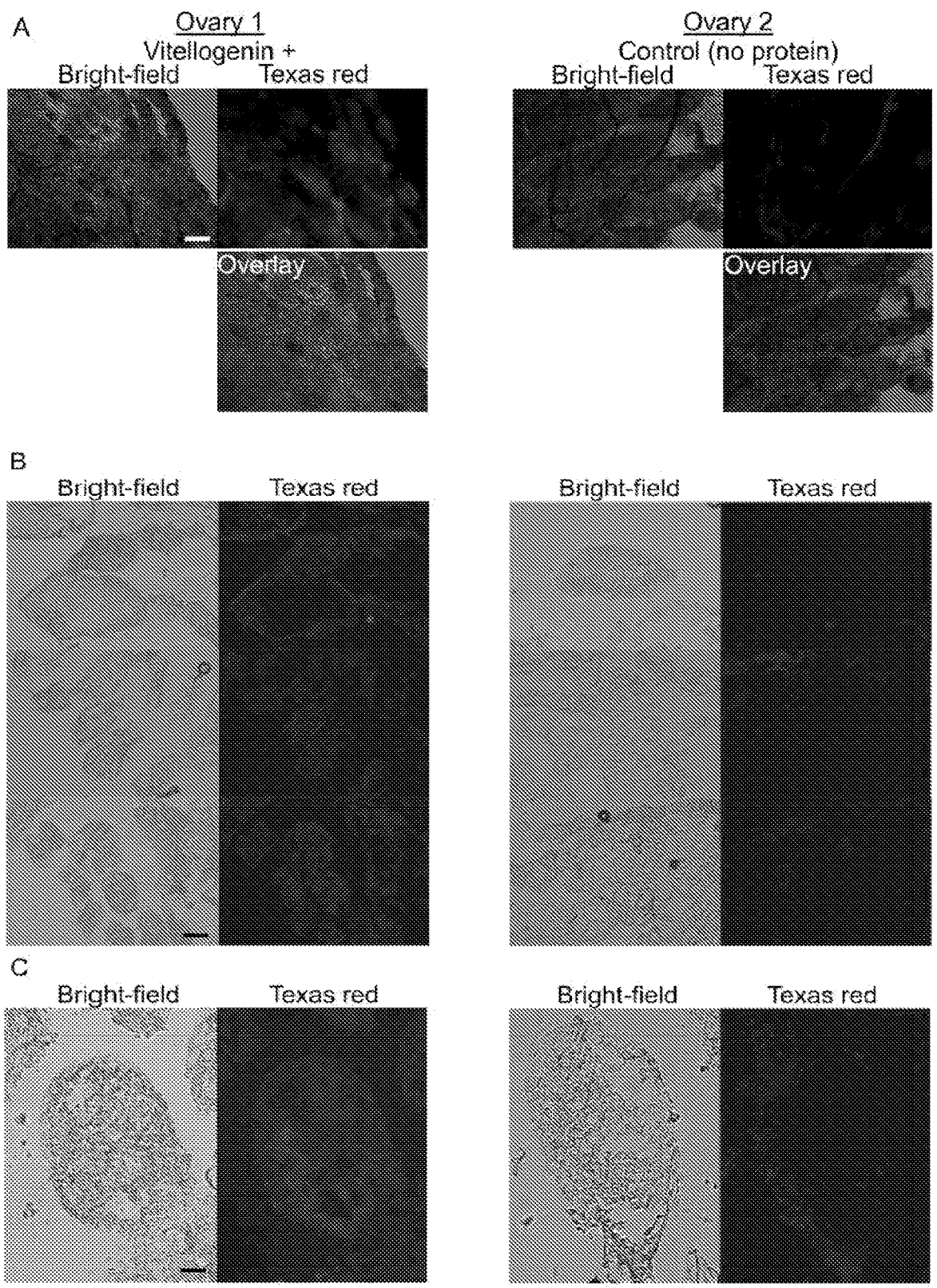

Next, we verified that Vg can carry pathogen-derived molecules into eggs. This was tested by incubating dissected honey bee queen ovaries with the commercially available fluorescently labeled *E. coli* fragments, followed by imaging the fluorescent material taken up by the ovarioles (ovarian filaments) in the absence and presence of purified Vg (FIG. 2). The uptake of bacterial material was found only in the eggs that were provided with Vg. This result is consistent with our proposition that Vg is a carrier of TGIP messages.

Co-localization of Vg and vaccine analogue (pieces of bacteria—*E. coli*) is shown in FIG. 10.

3. Vg is Sufficient and Necessary for TGIP

Figure 3:
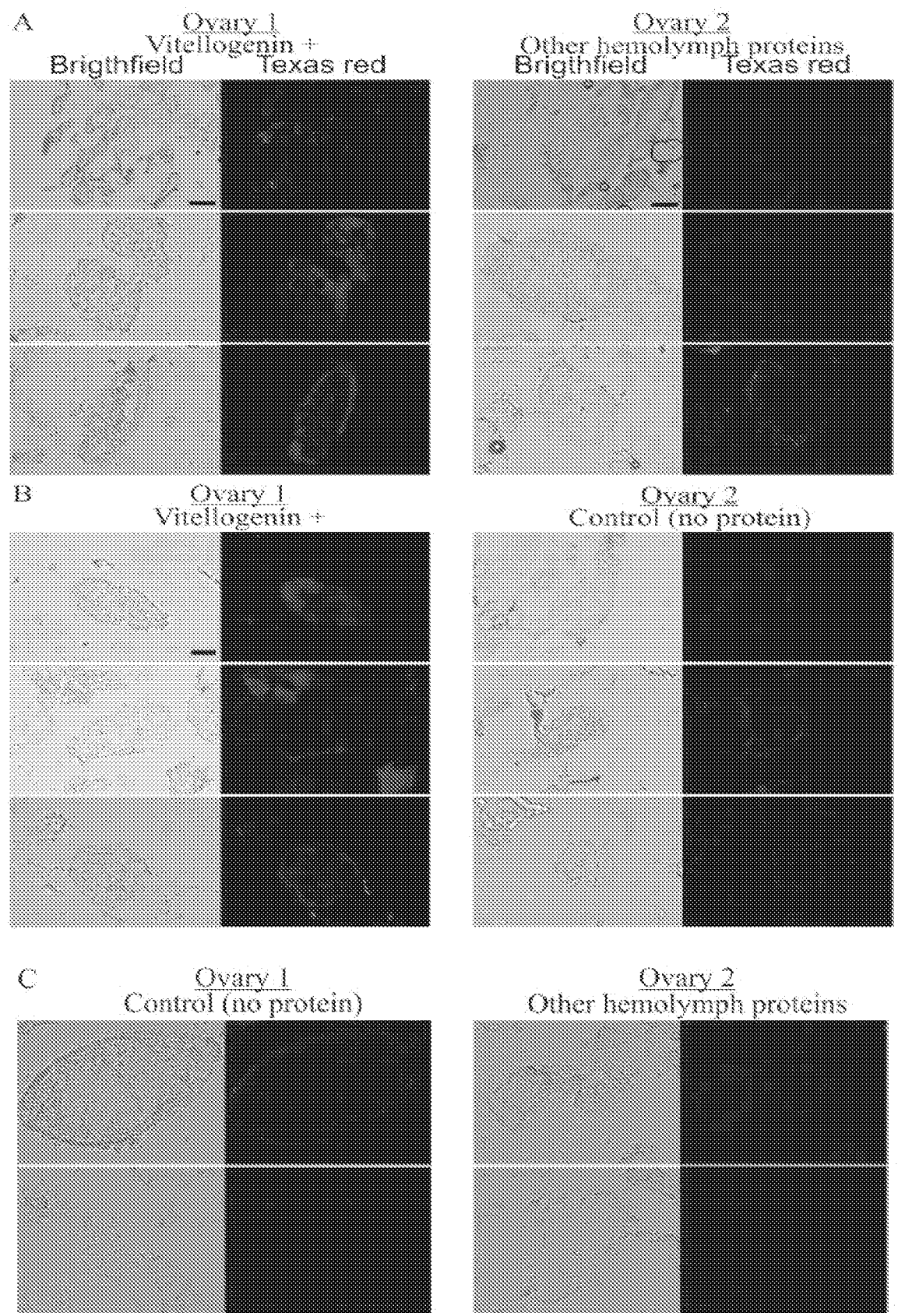

Finally, Vg was found to be a sufficient and necessary hemolymph protein for the transfer of immune elicitors to occur. To show this, we tested if the presence of other, non-Vg honey bee hemolymph proteins produced by ion-exchange fractioning of honey bee hemolymph can trigger the transfer of immune elicitors to the developing eggs. The major protein fractions in the samples of other proteins are apolipophorin and hexamerins that are involved in transport and storage functions (see S1 for an SDS-PAGE gel of hemolymph, pure Vg and the other non-Vg proteins, and a hemolymph fractioning chromatogram). In the case of the non-Vg hemolymph proteins, the result was negative (FIG. 3).

4. Vaccinated Beehives Show Higher Resistance to the *Paenibacillus larvae* Infection in the Larval Stage The vaccine fed to the queens prior to egg laying is to increase the survival of the larvae upon infection with *P. larvae* in a dose dependent manner. Vaccination is to be more successful against lower doses of spores (e.g. 90% survival in the case of 5 spores) in comparison to higher doses (e.g. 50% survival in the case of 20 spores), whereas in non-vaccinated hives almost all the larvae succumb to infection.

Similar results on any microbe disease or infection may be obtained by utilizing any corresponding bacteria, fungi, or fragments thereof or spores thereof in any insect species.

The invention claimed is:

1. A method of preventing American foulbrood disease or infection in a honey bee or a honey bee larvae caused by *Paenibacillus larvae* bacteria, wherein the method comprises feeding a honey bee queen with an artificial insect diet comprising dead *Paenibacillus larvae* bacteria, wherein said artificial insect diet acts as a vaccine against said American foulbrood disease or infection in the honey bee or the honey bee larvae.

2. The method according to claim 1, wherein said artificial insect diet is used as the only vaccine against said American foulbrood disease or infection.

3. The method according to claim 1, wherein the amount of bacteria in the artificial diet is 1 to 20% by weight.

4. The method according to claim 1, wherein the artificial diet is for administration one, two or three times a year.

5. The method according to claim 1, wherein amount of bacteria in the artificial diet is from 1 to 10% by weight.

6. A method for increasing the survival of an insect larvae upon infection with *Paenibacillus larvae* bacteria comprising feeding an insect queen prior to egg laying with an artificial insect diet comprising dead *Paenibacillus larvae* bacteria, wherein the insect queen is a honey bee queen and the insect larvae are the queen's honey bee larvae.

7. The method of claim 6, wherein the *Paencibacillus larvae* bacteria causes American foulbrood disease.

8. The method of claim 6, wherein amount of bacteria in the artificial diet is 1 to 20% by weight.

9. The method of claim 6, wherein the artificial diet is for administration one, two or three times a year.

10. The method of claim 6, wherein amount of bacteria in the artificial diet is from 1 to 10% by weight.

* * * * *